US00PP30422P3

(12) United States Plant Patent
Wheeler et al.

(10) Patent No.: US PP30,422 P3
(45) Date of Patent: Apr. 23, 2019

(54) BLUEBERRY PLANT NAMED 'BB06-507MI-52'

(50) Latin Name: *Vaccinium corymbosum*
Varietal Denomination: BB06-507MI-52

(71) Applicant: Berry Blue, LLC, Grand Junction, MI (US)

(72) Inventors: Edmund J. Wheeler, Holland, MI (US); James F. Hancock, Scarborough, ME (US)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 15/731,864

(22) Filed: Aug. 14, 2017

(65) Prior Publication Data

US 2018/0177090 P1 Jun. 21, 2018

Related U.S. Application Data

(63) Continuation of application No. 15/150,531, filed on May 10, 2016, now abandoned.

(51) Int. Cl.
*A01H 5/08* (2018.01)

(52) U.S. Cl.
USPC ..... Plt./157
CPC ..... *A01H 5/08* (2013.01)

(58) Field of Classification Search
USPC ..... Plt./157
See application file for complete search history.

*Primary Examiner* — Susan McCormick Ewoldt
(74) *Attorney, Agent, or Firm* — King IP Law; Joshua King

(57) ABSTRACT

A new and distinct cultivar of Blueberry plant named 'BB06-507MI-52' as described and shown. 'BB06-507MI-52' is a new and distinct high chill tetraploid Northern highbush blueberry (*Vaccinium*) variety of complex ancestry, based largely on *V. corymbosum* with small contributions of *V. darrowii, V. angustifolium, V. tenellum* and *V. ashei*. It is a very productive and very early ripening. It is characterized as having very large fruit with a very small and dry picking scar, medium blue color and very firm fruit with excellent eating and storage quality for the fresh market. The 'BB06-507MI-52' variety has very good flavor with a balanced amount of sugar and acidity and it is also very firm and juicy. Storage ability in refrigeration is excellent up to 6 weeks and longer with very little decline in quality.

3 Drawing Sheets

Latin name: *Vaccinium corymbosum.*

BACKGROUND AND SUMMARY

Blueberries are a well-known fruit enjoyed by many throughout the world. One example of an existing blueberry variety is 'Bluetta', an unpatented USDA release from 1961. Another example of an existing blueberry variety is 'Duke', an unpatented USDA release from 1967.

Compared to 'Bluetta', 'BB06-507MI-52' is 5 days later in maturity, much larger in size, has a much smaller and dry pedicel scar, is lighter in color, much firmer and has a slightly higher Brix° level.

Compared to 'Duke', 'BB06-507MI-52' is 5 days earlier in maturity, a much larger berry, lighter in color, much firmer and has a higher Brix° level.

The present cultivar, 'BB06-507MI-52', provides one or more advantages compared to these and/or other blueberry varieties.

BRIEF DESCRIPTION OF THE PHOTOGRAPHS

DETAILED DESCRIPTION

Figure 1:
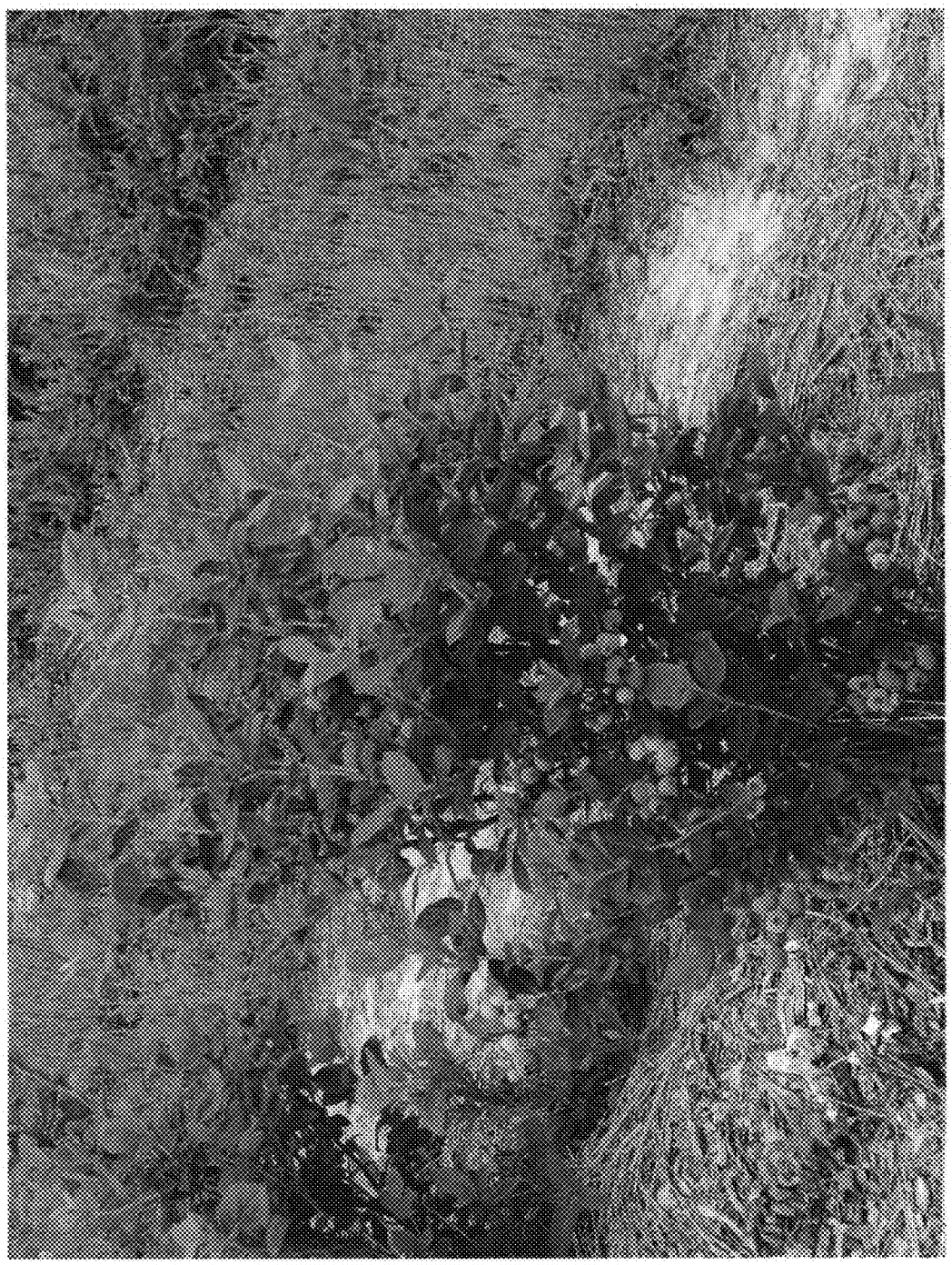
FIG. 1 is a photograph taken July 2015 in Grand Junction Mich. of the Blueberry cultivar BB06-507MI-52 showing a 3-year old plant and plant habit, branching, leaf color, unripe and ripe fruit.
Figure 2:
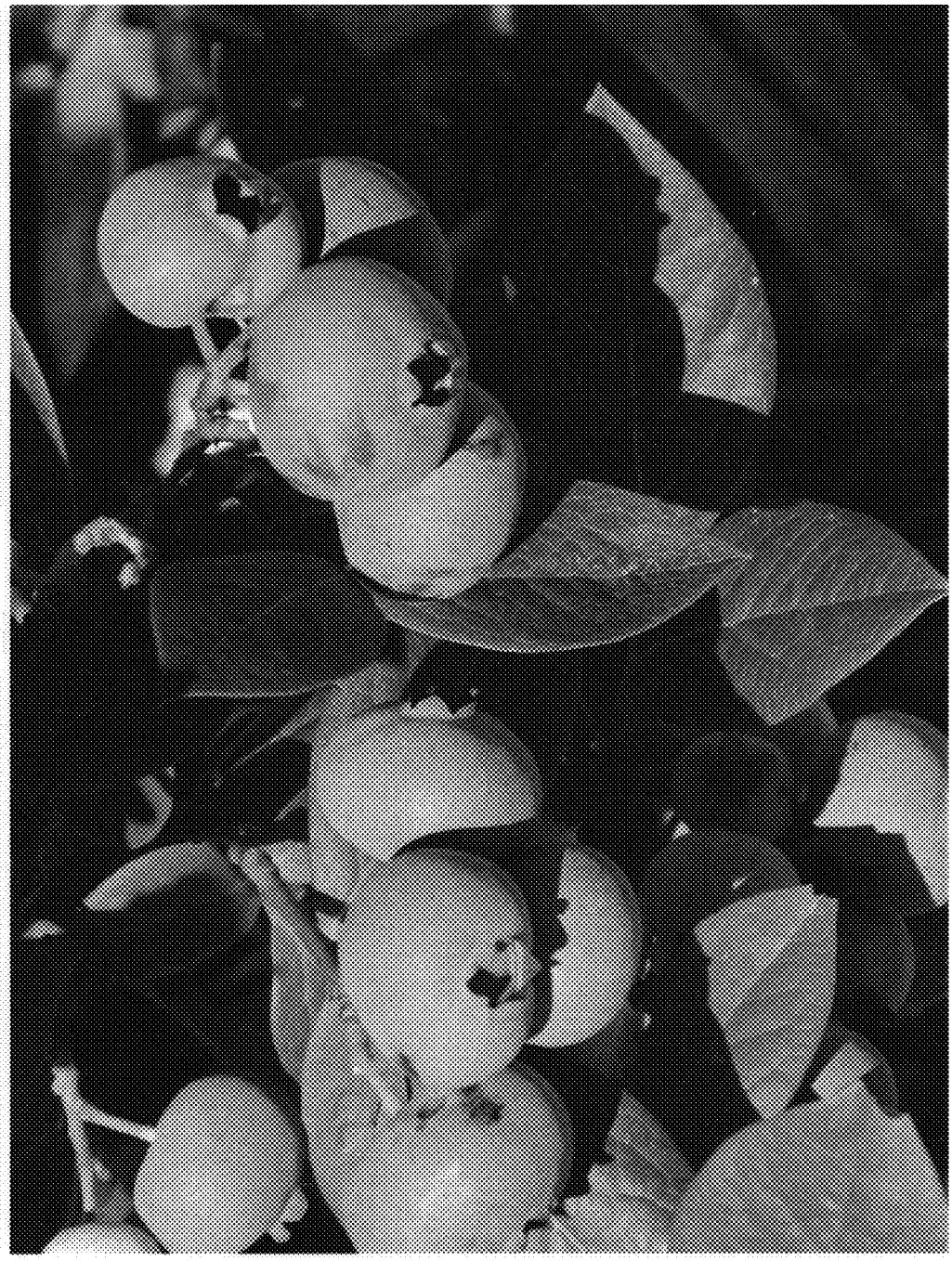
FIG. 2 is a close-up photograph taken July 2015 in Grand Junction Mich. of the Blueberry cultivar BB06-507MI-52, showing ripe fruit, fruit color, fruit shape, leaf shape and color and pedicels on a 3-year old plant.
Figure 3:
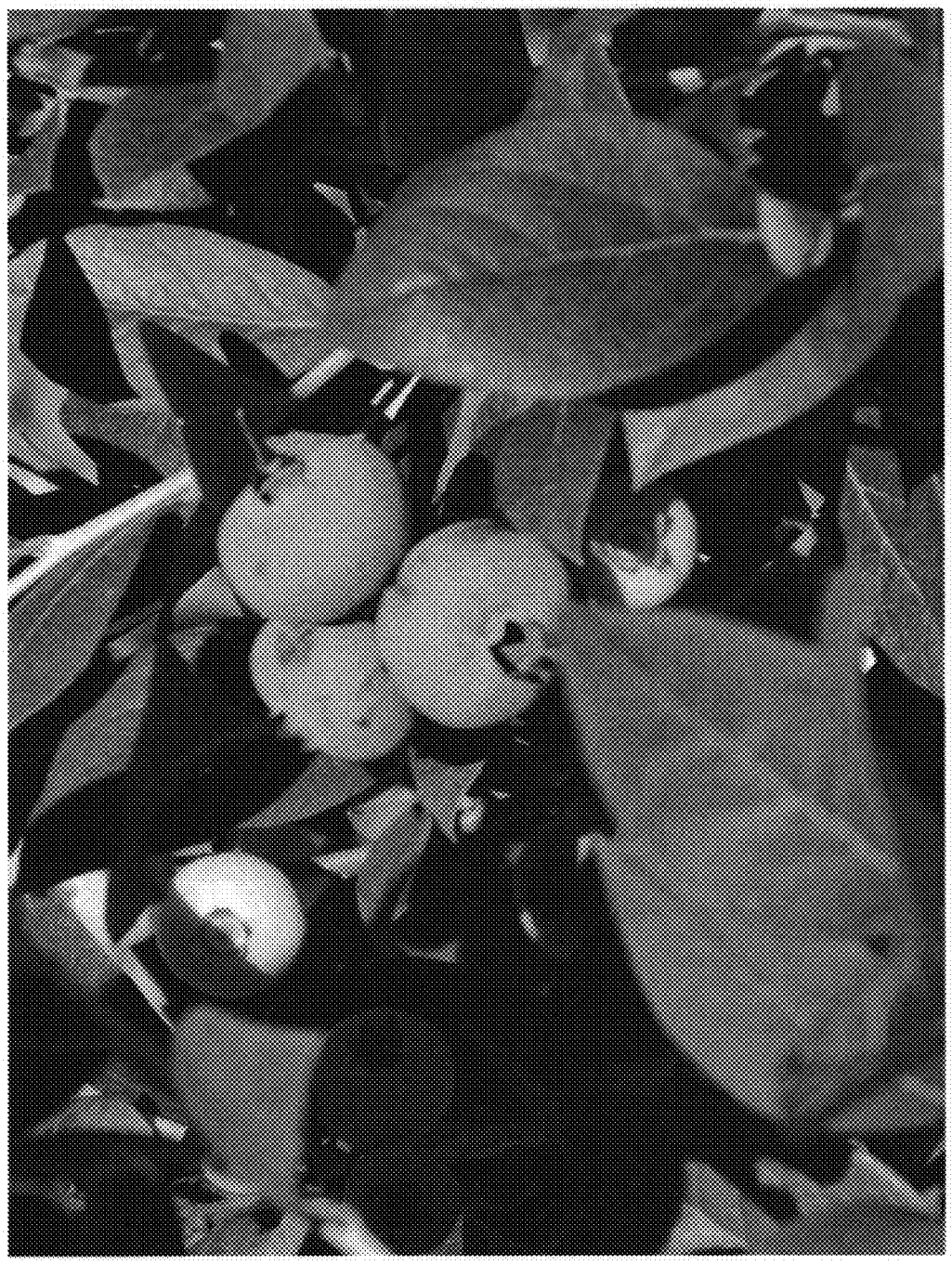
FIG. 3 is a close-up photograph taken July 2015 in Grand Junction Mich. of the Blueberry cultivar BB06-507MI-52, showing ripe and unripe fruit, fruit color both ripe and unripe and leaf shape and color on a 3-year old plant.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown near Grand Junction, Mich., South Haven, MIC, Bloomingdale, Mich. and Muskegon, Mich. in 2013-2015. Data were obtained on plants that were about 3-4 years old.

Cultivar name: 'BB06-507MI-52'.
Classification:
Family: Ericaceae.
Botanical name: *Vaccinium corymbosum.*
Common name: Blueberry.
Parentage:
Female Parent
Name: 'Draper'.
U.S. Plant Pat. No. 15,103.

Compared to 'Draper', 'BB06-507MI-52' has a maturity date that is 7 days earlier. 'BB06-507MI-52' has a rounder berry shape and slightly darker blue color than 'Draper'. 'BB06-507MI-52' also has a much larger size berry and a slightly lower level of Brix° compared to 'Draper'.

Male Parent

'Brigitta'.

U.S. Plant Pat. No.: Not patented.

Compared to 'Brigitta', 'BB06-507MI-52' matures 21 days earlier. 'BB06-507MI-52' has a much larger and much firmer berry than 'Brigitta'. 'BB06-507MI-52' has a lighter blue color, and a slightly lower level of Brix° than 'Brigitta'.

'BB06-507MI-52' originated as a seedling selected from the cross 'Draper' (female) x 'Brigitta' (male). The seed that gave rise to 'BB06-507MI-52' was produced by hand-pollination in a greenhouse in Grand Junction Mich. in 2006, grown for 18 months in Grand Junction Mich. and then shipped to South Haven Mich. where it was planted in an observation nursery in 2008. In 2010, 'BB06-507MI-52' was first selected for the desirable features of very early maturity, very large size, excellent fruit quality and long storage ability and was given the designation 'BB06-507MI-52'. 'BB06-507MI-52' was first asexually propagated by vegetative cuttings in Grand Junction, Mich. for further testing in 2010. Three to ten plants were placed in advanced test plots in South Haven, Bloomingdale, Mich. and Muskegon, Mich. in 2011 and 2012. 'BB06-507MI-52' was further observed in 2013 through 2015. The propagated plants have retained the original characteristics of the original selected plants when grown in Western Michigan.

'BB06-507MI-52' was first propagated by vegetative cuttings for further testing in 2010 in Grand Junction, Mich. Further vegetative cuttings have been taken several times since 2010 in Grand Junction, Mich. and tissue culture in Middleton, Wis. since 2012 as needed. In all cases the propagated plants have retained the original characteristics of the original selected plants when grown in Western Michigan. The variety roots readily from hardwood or softwood cuttings as well as tissue-cultured microshoots.

All field observations were made in 2014 and 2015 on plants located in advanced trials in Grand Junction, Mich., South Haven, Mich., Bloomingdale, Mich., and Muskegon, Mich. from plants propagated from the original selected plant. Laboratory analysis of fruit characteristics were done in Grand Junction Mich. in 2014 and 2015.

General comments: 'BB06-507MI-52' is a new and distinct high chill tetraploid Northern highbush blueberry (*Vaccinium*) variety of complex ancestry, based largely on *V. corymbosum* with small contributions of *V. darrowii, V. angustifolium, V. tenellum* and *V. ashei*. It is a very productive very early ripening variety. It is characterized as having very large fruit with a very small and dry picking scar, medium blue color and very firm fruit with excellent eating and storage quality for the fresh market. The variety has the characteristics of concentrated fruit ripening, upright bush shape, a small crown, easy detachment of very firm fruit for mechanical harvesting. It is suitable at least for areas that successfully grow high chill Northern highbush varieties. The fruit are large, typically 18 mm or more with an average berry weight of 3.2 grams per berry, well exposed on upright bushes with a small crown. The mean date of 50% flowering is May 12 in Grand Junction, Mich. Winter chill requirement for successful flowering and fruiting is approximately 800-1000 hours (<7° C.). Flowering and leafing are synchronous. The mean ripening date in Grand Junction is July 1. Fruit shape is oblate with a medium heavy amount of waxy bloom that is relatively persistent after handling. The variety has very good flavor with a balanced amount of sugar and acidity and it is also very firm and juicy. Storage ability in refrigeration is excellent up to 6 weeks and longer with very little decline in quality.

References to color refer to The Pantone Book of Color, Eisemann and Herbert, Harry N. Abrams, Inc. Publishers, New York, ISBN 0-8109-3711-5, 1990.

Color measurements were taken with a SpectraMagic NX Model CR410, Konica Minolta, Japan.

Morphological characteristics reference: Plant Systematics, Jones and Luchsinger, 2 Ed., McGraw Hill, New York, ISBN 0-07-032796-3, 1986.

Device used to measure Soluble Solids (SS-Brix°), Titratable acidity (TA), pH: PAL-BX/Acid 7, Atago USA, Inc., Bellevue, Wash.

Firmness readings—BioWorks FirmTec2, Wamena, Kans.

Average size information:

*General description.*—Medium large bush, very upright bush shape, a typical 4 year old plant has 107 cm height, 56 cm width, height/width ratio 1.91:1.

*Growth.*—Very good vigor, strong leafing, medium number of canes.

*Productivity.*—Very good.

*Cold hardiness.*—Leaf and flower buds −5° C., open flowers and fruit −2° C.

Specific features of the variety:

Plant:

*Growth habit.*—Very upright.

*Plant width.*—56 cm.

*Plant height.*—107 cm.

*Spread.*—56 cm.

*Productivity.*—6-7 lbs per mature bush.

*Cold hardiness/tolerance.*—Leaf and flower buds −5° C., open flowers and fruit −2° C.

*Chilling requirement.*—800-1000 hours below 7° C.

*Canes.*—Moderately branched, average 4 canes per bush, average 38 cm in length per cane, medium number of laterals.

*Mature cane color.*—Pantone Gray Sand 15-1225.

*Texture.*—Rough.

*Fruiting wood.*—Medium smooth, immature winter color — Pantone Baked Clay 18-1441, immature summer color — Pantone Tarragon 15-0326.

*Internode length range.*—13-18 mm range, average 16 mm.

*Surface texture of new wood.*—Smooth.

*Mature canes.*—Circular in shape, 15 mm in diameter.

*Time of beginning of leaf bud burst.*—April 25 (Grand Junction, Mich.).

*Time of beginning of flowering.*—May 5 (Grand Junction, Mich.).

*Time of fruit ripening.*—50% July 1 (Grand Junction, Mich.).

*Disease resistance/susceptibility.*—None claimed.

Foliage:

*Leaf color.*—Upper — Pantone Cypress 18-0322, Lower: Pantone Peridot 17-0336.

*Leaf arrangement.*—Simple Alternate.

*Leaf margins.*—Entire.

*Leaf venation.*—Pinnate.

*Leaf apices.*—Acute.

*Leaf bases.*—Acute.

*Vein and petiole coloration.*—Pantone Green Moss 17-0636.
*Petiole length.*—4 mm.
*Petiole diameter.*—1 mm.
*Fall leaf color.*—Pompeian Red 18-1658.
*Evergreen.*—No.

Leaf dimensions:
*Overall shape.*—Obtuse.
*Length.*—64 mm-70 mm range, average 67 mm.
*Width.*—43 mm-46 mm range, average 45 mm.
*Leaf margins.*—Entire, very few nectaries visible, no pubescence.
*Leaf surface.*—Smooth upper and lower, pubescence on basal midrib.

Flower buds:
*Shape.*—Elliptic.
*Length.*—6 mm.
*Width.*—3 mm.
*Color.*—Pantone Baked Clay 18-1441.

Flower:
*Flower shape.*—Urceolate.
*Flower bud number.*—Medium high.
*Flowers per cluster.*—5-6.
*Flower fragrance.*—None detected.
*Corolla color.*—Pantone Turtle Dove 12-5202.
*Corolla length.*—9 mm.
*Corolla width.*—4 mm.
*Corolla aperture width.*—5 mm.
*Corolla texture.*—Smooth.
*Flower peduncle length.*—5 mm.
*Peduncle diameter.*—1 mm.
*Peduncle texture.*—Slightly rought.
*Peduncle color.*—Pantone Spinach Green 16-0439.
*Flower pedicel length.*—4 mm.
*Pedicel diameter.*—1 mm.
*Pedicel texture.*—Smooth.
*Pedicel color.*—Pantone Spinach Green 16-0439.
*Calyx* (*with sepals*).—Width 3 mm.
*Calyx color.*—Pantone Spinach Green 16-0439.
*Stamen length.*—8 mm.
*Number per flower.*—10.
*Filament color.*—Pantone Burnt Orange 16-1448.
*Style.*—8 mm.
*Style color.*—Pantone Cedar 16-0526.
*Pistil.*—8 mm.
*Ovary color.*—Pantone Cedar 16-0526.
*Anther length.*—3 mm.
*Number.*—10.
*Color.*—Pantone Burnt Orange 16-1448.

Pollen:
*Abundance.*—Medium.
*Color.*—Pantone Antique White 11-0105.

Fruit:
*Date of 50% maturity.*—Jul. 1, 2015 (Grand Junction).
*Duration of ripening.*—13 days.
*Yield.*—6-7 lbs per bush.
*Immature fruit color.*—Pantone Epsom 17-0324.
*Berry color with wax.*—Pantone Velvet Morning 18-3927, SpectraMagic (L,a,b) — (40.76, 2.31, −1.07).
*Berry color with wax removed.*—Pantone Crown Blue 19-3926.
*Berry flesh color.*—Pantone Frozen Dew 13-0513.
*Berry surface wax abundance.*—Medium heavy, moderately persistent.
*Berry weight.*—3.2 grams/berry.
*Berry size.*—Height 14.5 mm, width 18.7 mm, aspect (H/W) 0.8.
*Berry shape.*—Oblate.
*Cluster density.*—Loose.
*Average number of fruit per cluster.*—8.
*Average weight of fruit per cluster.*—25 grams.
*Detachment force.*—Easy.
*Self-fruitfulness.*—Very good; cross pollination would enhance earliness and size potential.
*Fruit stem scar.*—1.5 mm diameter, 1 mm depth.
*Calyx.*—5 lobed, lobed prominently ridged and slightly curved inward, diameter 5 mm, depth 1 mm.
*Berry firmness.*—Very firm, FirmTec: 254 grams/mm.
*Berry sweetness.*—12.0.
*Berry acidity.—TA* 0.81, 3.2 pH.
*Berry flavor and texture.*—Very good, balanced sweetness and acidity, crunchy and juicy texture.
*Storage quality.*—Very long, 6+ weeks in refrigerated storage.
*Suitability for mechanical harvesting.*—Excellent, upright bush shape, medium crown size, very firm fruit on long pedicels, concentrated harvest.
*Uses.*—Fresh and frozen markets, processing into jams, puree, yogurt, dehydration.

Seed:
*Seed abundance in fruit.*—Moderate.
*Seed color.*—Pantone Copper Brown 18-1336.
*Seed dry weight.*—NA.
*Seed size.*—1.5 mm length×1.0 mm width.
*Possible typical market uses.*—Fresh and frozen markets, processing into jams, puree, yogurt, dehydration.

What is claimed is:

1. A new and distinct cultivar of Blueberry plant named 'BB06-507MI-52' as described and shown herein.

* * * * *